(12) United States Patent
Gustafson

(10) Patent No.: US 11,395,727 B2
(45) Date of Patent: **\*Jul. 26, 2022**

(54) GRAFT PREPARATION SYSTEM

(71) Applicant: Medos International Sárl, Le Locle (CH)

(72) Inventor: Adam Gustafson, Dighton, MA (US)

(73) Assignee: MEDOS INTERNATIONAL SÀRL, Le Locle (CH)

(\*) Notice: Subject to any disclaimer, the term of this patent is extended or adjusted under 35 U.S.C. 154(b) by 362 days.

This patent is subject to a terminal disclaimer.

(21) Appl. No.: 16/380,530

(22) Filed: Apr. 10, 2019

(65) Prior Publication Data

US 2019/0231516 A1 Aug. 1, 2019

Related U.S. Application Data

(62) Division of application No. 14/977,882, filed on Dec. 22, 2015, now Pat. No. 10,383,720.

(51) Int. Cl.
*A61F 2/08* (2006.01)
(52) U.S. Cl.
CPC ........ *A61F 2/08* (2013.01); *A61F 2240/001* (2013.01); *A61F 2240/002* (2013.01)
(58) Field of Classification Search
None
See application file for complete search history.

(56) References Cited

U.S. PATENT DOCUMENTS

| | | | |
|---|---|---|---|
| 4,143,426 A | 3/1979 | Hall et al. | |
| 4,469,101 A | 9/1984 | Coleman et al. | |
| 4,759,765 A | 7/1988 | Van Kampen | |
| 4,946,377 A | 8/1990 | Kovach | |

(Continued)

FOREIGN PATENT DOCUMENTS

| | | |
|---|---|---|
| DE | 202014007804 A1 | 10/2014 |
| EP | 2777613 A1 | 9/2014 |

(Continued)

OTHER PUBLICATIONS

U.S. Appl. No. 14/977,882, filed Dec. 22, 2015, Graft Preparation System.

(Continued)

*Primary Examiner* — Megan Y Wolf

(57) ABSTRACT

Systems and methods for preparing a ligament graft for a ligament reconstruction procedure are provided. In general, the described techniques utilize a graft holder construct having a graft preparation holder and a suture assembly removably coupled thereto. The graft preparation holder includes an elongate support rail having a longitudinal axis, and a plurality of leaf segments positioned along the longitudinal axis in a spaced relationship and extending laterally from the support rail. The leaf segments can bend to a graft holding configuration so as to define a graft receiving channel configured to receive a graft therethrough. The holder also has at least one support structure configured to mate with the leaf segments to provide stability and rigidity to the segments. The suture assembly has at least one suture tail that can be pulled to affix the suture assembly to a graft without penetrating the graft.

20 Claims, 8 Drawing Sheets

(56) References Cited

U.S. PATENT DOCUMENTS

| | | | |
|---|---|---|---|
| 4,979,956 A | 12/1990 | Silvestrini | |
| 5,061,283 A | 10/1991 | Silvestrini | |
| 5,144,961 A | 9/1992 | Chen et al. | |
| 5,281,422 A | 1/1994 | Badylak et al. | |
| 5,284,485 A | 2/1994 | Kammerer et al. | |
| 5,306,301 A | 4/1994 | Graf et al. | |
| 5,372,821 A | 12/1994 | Badylak et al. | |
| 5,456,721 A | 10/1995 | Legrand | |
| 5,527,341 A | 6/1996 | Gogolewski et al. | |
| 5,540,703 A | 7/1996 | Barker, Jr. et al. | |
| 5,573,784 A | 11/1996 | Badylak et al. | |
| 5,628,756 A | 5/1997 | Barker, Jr. et al. | |
| 5,645,588 A | 7/1997 | Graf et al. | |
| 5,769,862 A | 6/1998 | Kammerer et al. | |
| 5,800,543 A | 9/1998 | McLeod et al. | |
| 6,056,752 A | 5/2000 | Roger | |
| 6,080,184 A * | 6/2000 | Peters | A61B 17/06133 206/63.3 |
| 6,083,244 A | 7/2000 | Lubbers et al. | |
| 6,102,947 A | 8/2000 | Gordon | |
| 6,106,556 A | 8/2000 | Demopulos et al. | |
| 6,143,029 A | 11/2000 | Rippstein | |
| 6,203,572 B1 | 3/2001 | Johnson et al. | |
| 6,260,696 B1 * | 7/2001 | Braginsky | A61B 17/06133 206/380 |
| 6,296,659 B1 | 10/2001 | Foerster | |
| 6,322,571 B1 | 11/2001 | Adams | |
| 6,342,060 B1 | 1/2002 | Adams | |
| 6,602,290 B2 | 8/2003 | Esnouf et al. | |
| 6,821,286 B1 | 11/2004 | Carranza et al. | |
| 7,371,253 B2 | 5/2008 | Leung et al. | |
| 7,465,308 B2 | 12/2008 | Sikora et al. | |
| 7,892,256 B2 | 2/2011 | Grafton et al. | |
| 8,202,318 B2 | 6/2012 | Willobee | |
| 8,231,654 B2 | 7/2012 | Kaiser et al. | |
| 8,298,247 B2 | 10/2012 | Sterrett et al. | |
| 8,298,284 B2 | 10/2012 | Cassani | |
| 8,403,947 B2 | 3/2013 | Ochiai | |
| 8,439,936 B2 | 5/2013 | McClellan | |
| 8,460,350 B2 | 6/2013 | Albertorio et al. | |
| 8,500,809 B2 | 8/2013 | Saliman | |
| 8,562,645 B2 | 10/2013 | Stone et al. | |
| 8,574,296 B2 | 11/2013 | Missos | |
| 8,591,544 B2 | 11/2013 | Jolly et al. | |
| 8,591,578 B2 | 11/2013 | Albertorio et al. | |
| 8,652,172 B2 | 2/2014 | Denham et al. | |
| 8,663,324 B2 | 3/2014 | Schmieding et al. | |
| 8,690,960 B2 | 4/2014 | Hotter et al. | |
| 8,888,848 B2 | 11/2014 | Saliman et al. | |
| 9,011,533 B2 | 4/2015 | Gadikota et al. | |
| 9,060,854 B2 | 6/2015 | Altman et al. | |
| 9,101,462 B2 | 8/2015 | Miller | |
| 9,993,332 B2 | 6/2018 | Woodruff et al. | |
| 10,357,355 B2 | 7/2019 | Woodruff et al. | |
| 2003/0050668 A1 | 3/2003 | Lee | |
| 2003/0130735 A1 | 7/2003 | Rogalski | |
| 2007/0123984 A1 | 5/2007 | Hodorek | |
| 2007/0239275 A1 | 10/2007 | Willobee | |
| 2007/0250163 A1 | 10/2007 | Cassani | |
| 2007/0288023 A1 | 12/2007 | Pellegrino et al. | |
| 2007/0288040 A1 | 12/2007 | Ferree | |
| 2008/0188936 A1 | 8/2008 | Ball et al. | |
| 2009/0018655 A1 | 1/2009 | Brunelle et al. | |
| 2009/0105754 A1 | 4/2009 | Sethi | |
| 2009/0228021 A1 | 9/2009 | Leung | |
| 2009/0306688 A1 | 12/2009 | Patel et al. | |
| 2009/0318958 A1 | 12/2009 | Ochiai | |
| 2010/0145367 A1 | 6/2010 | Ratcliffe | |
| 2010/0179591 A1 | 7/2010 | Saltzman et al. | |
| 2010/0222792 A1 | 9/2010 | Bames et al. | |
| 2010/0249802 A1 | 9/2010 | May et al. | |
| 2011/0015735 A1 | 1/2011 | Persson | |
| 2011/0160749 A1 | 6/2011 | Gordon et al. | |
| 2011/0238179 A1 | 9/2011 | Laurencin et al. | |
| 2012/0046746 A1 | 2/2012 | Konicek | |
| 2012/0239145 A1 | 9/2012 | Peterson et al. | |
| 2012/0253465 A1 | 10/2012 | Missos | |
| 2013/0013065 A1 | 1/2013 | Bills | |
| 2013/0023907 A1 | 1/2013 | Sterrett et al. | |
| 2013/0023927 A1 | 1/2013 | Cassani | |
| 2013/0116730 A1 | 5/2013 | Denham et al. | |
| 2013/0123937 A1 | 5/2013 | Jamiolkowski et al. | |
| 2013/0274879 A1 | 10/2013 | Champagne et al. | |
| 2013/0296936 A1 | 11/2013 | Burkhart | |
| 2014/0024885 A1 | 1/2014 | Sudekum | |
| 2014/0074239 A1 | 3/2014 | Albertorio et al. | |
| 2014/0163586 A1 | 6/2014 | Holt | |
| 2014/0243891 A1 | 8/2014 | Schmieding et al. | |
| 2014/0257346 A1 | 9/2014 | Sengun et al. | |
| 2014/0257384 A1 | 9/2014 | Dreyfuss et al. | |
| 2014/0277448 A1 | 9/2014 | Guerra et al. | |
| 2014/0350675 A1 | 11/2014 | Hackney et al. | |
| 2015/0025552 A1 | 1/2015 | Stoll | |
| 2015/0039030 A1 | 2/2015 | Saliman et al. | |
| 2015/0051700 A1 | 2/2015 | Collette | |
| 2015/0057750 A1 | 2/2015 | Timmerman | |
| 2015/0066059 A1 | 3/2015 | Sinnott et al. | |
| 2015/0073441 A1 | 3/2015 | Fallin et al. | |
| 2015/0134060 A1 | 5/2015 | Chudik | |
| 2015/0201924 A1 | 7/2015 | Gordon et al. | |
| 2015/0201925 A1 | 7/2015 | Benavitz | |
| 2015/0216542 A1 | 8/2015 | Libby et al. | |
| 2015/0238318 A1 | 8/2015 | McCullen | |
| 2015/0245831 A1 | 9/2015 | Sullivan | |
| 2015/0245841 A1 | 9/2015 | Linder et al. | |
| 2016/0008123 A1 * | 1/2016 | Woodruff | A61F 2/08 112/475.08 |
| 2017/0172725 A1 | 6/2017 | Gustafson | |
| 2019/0328505 A1 | 10/2019 | Woodruff et al. | |

FOREIGN PATENT DOCUMENTS

| | | |
|---|---|---|
| EP | 2923672 A1 | 9/2015 |
| JP | 2001506902 A | 5/2001 |
| JP | 2011522590 A | 8/2011 |
| WO | 9827894 A1 | 7/1998 |

OTHER PUBLICATIONS

U.S. Appl. No. 14/327,358, filed Jul. 9, 2014, Systems and Methods for Ligament Graft Preparation.
U.S. Appl. No. 15/994,000, filed May 31, 2018, Systems and Methods for Ligament Graft Preparation.
U.S. Appl. No. 16/444,809, filed Jun. 18, 2019, Systems and Methods for Ligament Graft Preparation.
European Search Report for Application No. 15176016.2, dated Nov. 9, 2015. (7 pages).
European Search Report for Application No. 16205252.6 dated May 12, 2017.

* cited by examiner

GRAFT PREPARATION SYSTEM

CROSS REFERENCE TO RELATED APPLICATIONS

The present application is a divisional of U.S. patent application Ser. No. 14/977,882, now U.S. Pat. No. 10,383,720, and entitled "Graft Preparation System" filed Dec. 22, 2015, which is hereby incorporated by reference in its entirety.

FIELD

The present disclosure relates to a system and method for graft preparation.

BACKGROUND

A ligament is a piece of fibrous tissue which connects one bone to another within the body. Ligaments are frequently damaged (e.g., detached, torn or ruptured) as the result of injury or accident. A damaged ligament can impede proper motion of a joint and cause significant pain. A damaged ligament can be replaced or repaired using various procedures, a choice of which can depend on a particular ligament to be restored and on the extent of the damage. When ligaments are damaged, surgical reconstruction can be necessary, as the ligaments may not regenerate on their own. An example of a ligament that is frequently damaged as a result of injury, overexertion, aging and/or accident is the anterior cruciate ligament (ACL) that extends between a top of the tibia and a bottom of the femur. A damaged ACL can cause instability of the knee joint, arthritis, and substantial pain.

ACL repair typically includes the use of a ligament graft replacement procedure which usually involves drilling a bone tunnel through the tibia and up into the femur. Then a ligament graft, which may be an artificial ligament or harvested graft, such as a tendon, is passed through a tibial portion of the tunnel (sometimes referred to as "the tibial tunnel") across the interior of the joint, and up into a femoral portion of a tunnel (sometimes referred to as "the femoral tunnel"). One end of the ligament graft can then be secured in the femoral tunnel and another end of the graft is secured in the tibial tunnel, at the sites where the natural ligament attaches.

Another ligament that is often damaged and may need to be replaced is a posterior cruciate ligament (PCL).

A common ligament reconstruction procedure involves using an autograft, which is a patient's own tendon that would replace the damaged natural ligament. The autograft is often a hamstring tendon, though other tendons can be used (e.g., a patellar tendon). The ligament graft can also be obtained from a donor ("allograft").

Ligament augmentation and replacement procedures typically require preparation of a harvested ligament graft using various techniques to secure the graft for passing through the drilled tunnels and to strengthen the graft prior to fixation. The preparation may involve cleaning and measuring the graft, and then affixing sutures to free ends thereof. The thus prepared graft can be tensioned prior to being inserted into the femoral and tibial tunnels.

Existing techniques for graft preparation, e.g., a conventional whip-stitching (simple or locking, typically involve passing a needle (not shown) or other suture passing instrument through a graft to create stitches. Such techniques can have certain drawbacks. For example, they may cause trauma to the graft and undesirable excessive elongation of the graft when a load is applied thereto. This can compromise the quality of the graft and create a risk of complications during the ligament reconstruction procedure. Other existing graft preparation techniques include, for example, baseball stitching, roman sandal suture techniques, krackow and Prusik knots.

The conventional approaches to graft preparation can be labor- and time-consuming and may take up a large portion of time during a reconstruction surgery. Placing a suture on the graft can be cumbersome and, when a graft is prepared using such techniques, the entire reconstruction procedure may be put on hold, which can contribute to increased costs of the surgery. In addition, the surgeon or other medical personnel sewing the stitches bears a risk of a needle-stick injury which can lead to potential infections.

Accordingly, there is a need for improved techniques and devices for preparing grafts.

SUMMARY

In some aspects, a graft preparation holder device is provided that can include an elongate support rail having a longitudinal axis and first and second ends, and a plurality of leaf segments positioned along the longitudinal axis in a spaced relationship and extending laterally from the support rail. Each leaf segment can have an attachment end at the support rail and an opposite, terminal end. Each leaf segment can be bendable at a bending portion disposed between the attachment end and the terminal end of each leaf segment. Also, each leaf segment can have an inner surface and an outer surface and can be configured to bend along at least the bending portion thereof to a graft holding configuration in which the terminal ends of the leaf segments are in proximity to the attachment ends of the leaf segments to form a holder having a graft receiving channel defined by the inner surfaces of the leaf segments.

The graft preparation holder device can vary in any number of ways. For example, a first leaf segment extending from the support rail adjacent to the second end of the support rail can have first and second support panels extending therefrom in a direction parallel to the longitudinal axis. The first and second support panels can be disposed on opposite sides of the bending portion of the first leaf segment and each can be coupled to the first leaf segment via a coupling portion. Each of the first and second support panels can have inner and outer surfaces, and the panels can be configured to bend about the coupling portion such that the inner surfaces of the support panels mate with the outer surfaces of the leaf segments in the graft holding configuration. As another example, the bending portion of one or more of the leaf segments can be a living hinge. As a further example, the elongate support rail can be configured to seat adjacent thereto a suture spine having a plurality of windings coupled thereto.

Each leaf segment can have at least one first mating feature configured to mate with a complementary second mating feature formed on the inner surfaces of the first and second support panels. The at least one first mating feature can be in the form of at least one female receiver and the at least one second mating feature can be in the form of at least one male member.

One or more of the leaf segments can have various features coupled thereto or formed thereon. For example, the first leaf segment extending from the support rail adjacent to the second end of the support rail can have a first spacing element and a complementary second spacing element. The first and second spacing elements can extend from the first leaf segment in a direction perpendicular to the longitudinal axis such that the first and second spacing elements are disposed on opposite sides of the bending portion of the first leaf segment. The first and second spacing elements can be configured to mate when the holder is formed.

In some embodiments, a last leaf segment extending from the support rail adjacent to the first end of the support rail can have a third spacing element and a complementary fourth spacing element extending from the last leaf segment in a direction perpendicular to the longitudinal axis such that the third and fourth spacing elements are disposed on opposite sides of the bending portion of the last leaf segment.

In other aspects, a graft holder construct is provided that can include a graft holder having a graft receiving configuration. In the graft receiving configuration, the graft holder includes an elongate support rail having a longitudinal axis and first and second ends, a plurality of flexible leaf segments positioned along the longitudinal axis in a spaced relationship and extending laterally from the support rail, a suture spine removably seated adjacent to the support rail along the longitudinal axis, and a plurality of windings formed from a suture and spaced longitudinally along the suture spine. Each winding can be coupled to the spine and can be removably passed between adjacent leaf segments. Each leaf segment can have an attachment end at the support rail and an opposite, terminal end. The leaf segments can be bent to assume an arc-like shape when the graft holder is in a graft holding configuration to position the terminal ends of the leaf segments and the attachment ends of the leaf segments in closer proximity to one another to define a graft receiving channel.

The graft holder construct can vary in any number of ways. For example, the graft receiving channel can be configured to receive and retain a graft therein when the graft preparation holder is in the graft holding configuration. For another example, the suture forming the plurality of windings can have at least one tail end extending from the suture spine adjacent to the second end of the support rail and configured to be pulled to affix the plurality of windings to the graft when the graft is positioned in the graft receiving channel. For another example, the windings can form a criss-crossing pattern along an inner surface of the graft receiving channel.

The graft holder construct can further include at least one support structure coupled to the plurality of leaf segments. The at least one support structure can include first and second support panels mated to outer surfaces of the leaf segments the first and second support panels being adjacent to one another and being disposed on opposite sides of a substantially midpoint of the leaf segments.

In other aspects, a method of preparing a graft for a surgical procedure is provided that can include positioning a graft holder construct around a portion of the graft. The graft holder construct can include a bendable elongate holder and a suture assembly removably coupled to the holder. The bendable elongate holder can include an elongate support rail having a longitudinal axis and first and second ends, and a plurality of flexible leaf segments positioned along the longitudinal axis in a spaced relationship and extending laterally from the support rail. The suture assembly can include a suture spine positioned adjacent to the elongate support rail, a plurality of windings that are spaced longitudinally along the suture spine such that the windings are coupled to the spine and pass through lateral slots formed between the leaf segments, and a suture tail end extending from the suture spine. The method further includes changing a configuration of the bendable elongate holder so as to define a graft receiving channel formed by the leaf segments and to secure the graft holder construct around the portion of the graft, and pulling the tail end to affix the suture assembly to the portion of the graft such that the plurality of windings are secured around the portion of the graft without penetrating the graft and the windings are spaced apart along a length of the portion of the graft.

The method can vary in any number of ways. For example, the graft holder construct can be configured such that, when the windings are secured around the portion of the graft, the elongate holder separates from the suture assembly. As another example, changing a configuration of the bendable elongate holder so as to define the graft receiving channel includes causing each leaf segment to bend.

Each leaf segment can have an attachment end at the support rail and an opposite, terminal end. Each leaf segment can be bendable at a bending portion disposed between the attachment end and the terminal end of each leaf segment. The method can further include forming the bendable elongate holder by causing each leaf segment to bend along at least the bending portion thereof such that the terminal ends of the leaf segments are in proximity to the attachment ends of the leaf segments.

In some embodiments, securing the graft holder construct around the portion of the graft includes retaining the portion of the graft between first and second spacers extending from a terminal leaf segment.

BRIEF DESCRIPTIONS OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
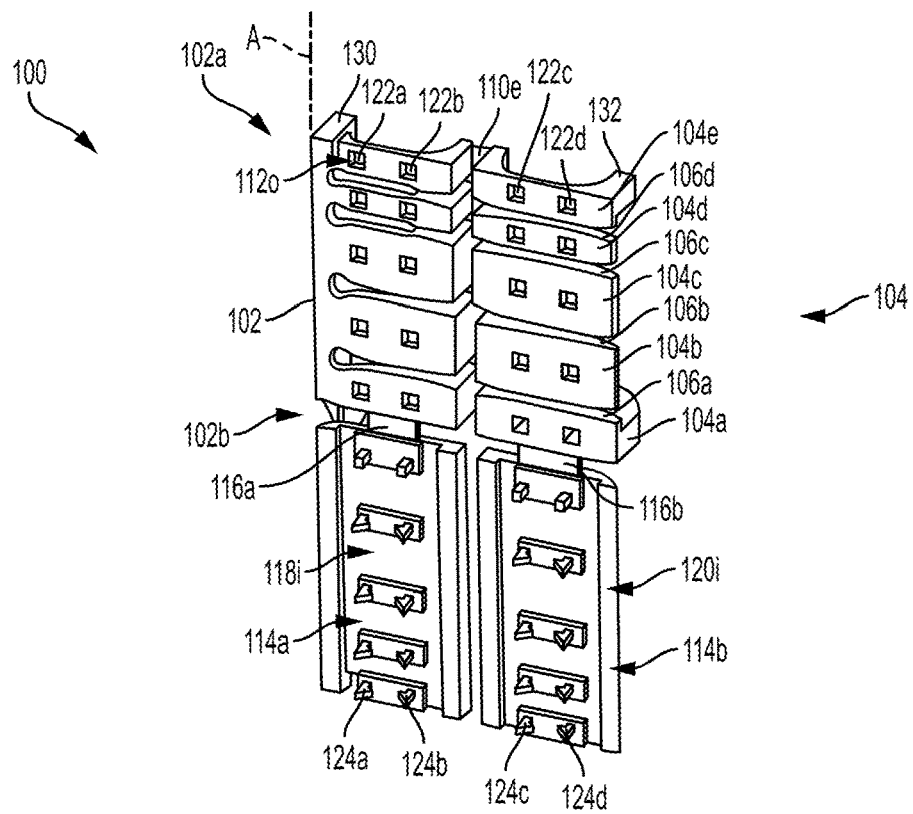
FIG. 1 is a perspective view of a one embodiment of a graft preparation holder device.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to systems and methods for preparing ligament grafts for ligament reconstruction or augmentation surgeries. In some embodiments, a bendable graft preparation holder includes an elongate support rail having a longitudinal axis and first and second ends and a plurality of leaf segments positioned along the longitudinal axis in a spaced relationship and extending laterally from the support rail. Each of the leaf segments has an attachment end at the support rail and an opposite, terminal end. The leaf segments are bendable at their bending portions disposed between the attachment and terminal ends of each leaf segment.

A graft holder construct is formed by removably retaining a suture assembly on the graft preparation holder. The suture assembly encompasses a suture spine removably seated adjacent to the support rail along the longitudinal axis thereof and a plurality of suture windings spaced longitudinally along the suture spine such that each winding is coupled to the spine and removably passes between adjacent leaf segments. A support structure can be coupled to the leaf segments to provide rigidity to the holder and to protect the suture windings from being inadvertently pinched or otherwise damaged during graft preparation. The graft holder construct can be placed in a pre-deployment configuration which significantly reduces the time required to affix sutures to the graft.

The graft holder construct is used to deliver the suture assembly to the graft by changing the pre-deployment configuration of the holder construct to a graft holding configuration in which the holder defines a graft receiving channel. To do so, the leaf segments are bent along at least their bending portions to bring the attachment and terminal ends of each leaf segment in proximity to one another, to thereby define the graft receiving channel. As the graft receiving channel is maintained (e.g., when a surgeon is holding the graft preparation holder), the suture assembly can be manipulated to affix the suture to the graft and then separate the suture from the holder.

The systems and methods described herein may have a number of advantages. In particular, the entire graft preparation procedure can be made more efficient, requiring a surgeon to take only a few quick steps to affix the delivery suture assembly to the graft. Because the suture is delivered to the graft without penetrating the graft, a risk of causing trauma to the graft is reduced. Also, a time required to prepare the graft is significantly reduced, which can facilitate the surgery and mitigate inconvenience to the patient. Because a pre-assembled construct is utilized, the reproducibility of the procedure is improved. Thus, the described graft preparation procedure is simplified and is less labor-intensive, which improves efficiency of the ligament reconstruction procedure, and mitigates risks posed by conventional time-consuming and less reliable graft preparation techniques. In addition, the described techniques can help to save operating room costs.

The described techniques can be used in conjunction with a variety of ligament grafts, including hamstring ligament grafts, and in a variety of different surgical contexts regardless of the type of ligament graft being used in a particular surgical procedure. The systems and methods described herein can be utilized in connection with preparing graft ligaments for repairing or replacing ligaments in a variety of joints, but they are particularly useful in cruciate ligament reconstruction procedures. In some embodiments, the systems and methods described herein are utilized for preparing ligament grafts for reconstruction procedures such as, for example, the cruciate ligaments of the knee or for distal biceps repair.

Figure 2:
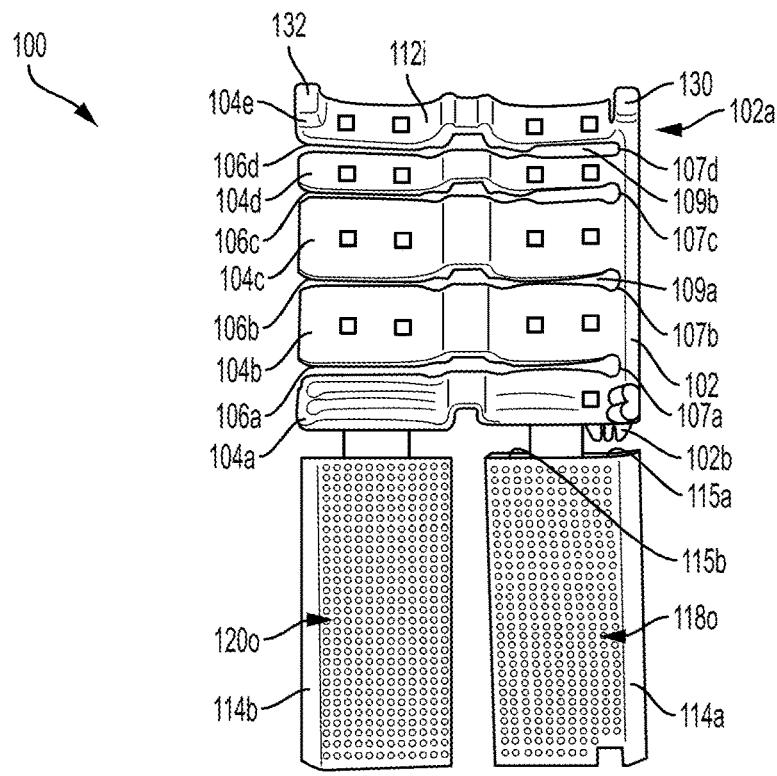
FIG. 2 is another perspective view of the graft preparation holder device of FIG. 1.
Figure 3:
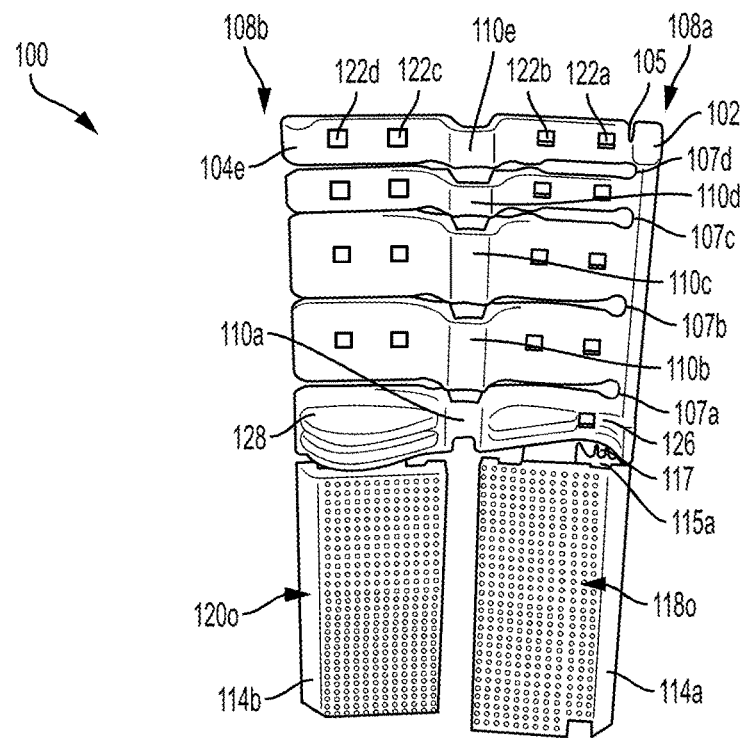
FIG. 3 is another perspective view of the graft preparation holder device of FIG. 1.

FIGS. 1-3 show one embodiment of a graft preparation holder 100. The graft preparation holder 100 is illustrated in FIGS. 1-3 in an unassembled configuration prior to loading the device 100 with suture so as to form a graft holder construct. The graft preparation holder 100 can be used by a surgeon in a pre-deployment configuration, after it is loaded with a suture spine and suture windings coupled thereto and assembled to removably retain the spine and windings, as discussed below.

As shown, the graft preparation holder 100 includes an elongate support rail 102 and a plurality of leaf segments 104 extending laterally from the support rail 102. The support rail 102 has a longitudinal axis A and first and second ends 102a, 102b. The support rail 102 is configured to seat adjacent thereto a suture spine having a plurality of windings coupled thereto, as discussed in more detail below.

In the example illustrated, the plurality of leaf segments 104 extending from the support rail 102 include five leaf segments individually labeled as 104a, 104b, 104c, 104d, 104e. However, it should be appreciated that the graft preparation holder can have any other number of leaf segments. The leaf segments 104a, 104b, 104c, 104d, 104e are positioned along the longitudinal axis A of the support rail 102 in a spaced relationship, such that slots 106a, 106b, 106c, 106d are formed between adjacent leaf segments. Each leaf segment 104 has an attachment end at the support rail 102 and an opposite, terminal end. Thus, as shown in FIG. 3 for a leaf segment 104e, the leaf segment 104e has an attachment end 108a at the support rail 102 and an opposite, terminal end 108b. In a graft holding configuration in which the leaf segments are bent to assume an arc-like shape, as shown, for example, in FIG. 4 below, the terminal ends of the leaf segments are in closer proximity to the attachment ends of the leaf segments to form a holder having a graft receiving channel, as discussed in more detail below.

In the illustrated example, the leaf segments 104a, 104b, 104c, 104d, 104e have different widths measured along an axis parallel to the longitudinal axis A of the support rail 102, such that the width of the leaf segment 104a is less than the widths of the leaf segments 104b, 104c, and the widths of the leaf segments 104d, 104e are less than the width of the leaf segment 104a. The widths of the leaf segments 104a, 104b, 104c, 104d, 104e define distances between the slots 106a, 106b, 106c, 106d which, in turn, define distances between the suture windings to be delivered to a graft using the graft preparation holder 100 when it is loaded with the suture. Thus, the suture windings extending through the slots 106c, 106d can be formed closer to each other than the suture windings extending through the slots 104a, 104b. A person skilled in the art will appreciate that the leaf segments 104a, 104b, 104c, 104d, 104e are shown in FIGS. 1-3 by way of example only, and that they can have the same widths or widths that vary in different ways. The lengths of the leaf segments 104a, 104b, 104c, 104d, 104e, which are measured along an axis perpendicular to the longitudinal axis A, can be the same or approximately the same. The thickness of the leaf segments 104a, 104b, 104c, 104d, 104e, can vary along the lengths of the leaf segments 104a, 104b, 104c, 104d, 104e.

One or more of the leaf segments 104 can have suture-retaining elements. For example, as shown in FIGS. 2 and 3, the leaf segment 104e has a cleat 105 configured to removably retain a suture spine such that the suture spine is taut during use and can withstand loads applied thereto during delivery of the spine and windings coupled thereto from the holder to a portion of the graft. At the same time, the cleat 105 allows for an easy release of the suture spine from the holder. As a person skilled in the art will appreciate, the leaf segment 104e can have other suture-retaining elements additionally or alternatively. Furthermore, although not present in the illustrated example, other leaf segments can have one or more suture-retaining elements.

The slots 106a, 106b, 106c, 106d between the adjacent leaf segments, which are configured to retain suture windings extending therethrough, can have a variety of different configurations. In the example illustrated, the leaf segments 104 are configured such that the slots' widths are appropriate (e.g., sufficiently narrow) to retain suture windings therein. A shape of each slot varies along its length. For example, as shown in FIGS. 1-3, the slots 106a, 106b, 106c, 106d have rounded portions 107a, 107b, 107c, 107d adjacent the support rail 102, which allow for easy passage of a needle (or another suture-passing device) with a suture attached thereto during assembly of the graft preparation holder 100 into a graft holder construct. It should be appreciated that the portions 107a, 107b, 107c, 107d can have other shapes and that the size of these portions can vary. The opposite ends of the slots can have sloped surface(s), e.g., in the form of chamfers that, during assembly of a graft preparation construct, facilitate guiding of the suture within the slots and prevent the suture from being caught on slot transitions.

As also shown, portions of the slots disposed farther away from the portions 107a, 107b, 107c, 107d are more narrow and substantially uniform throughout the lengths of the slots. As shown, the slots 106a and 106b become narrow at a distance away from the rounded portions 107a, 107b that is less than a distance of narrow portions of slots 106c and 106d from their respective rounded portions 107c, 107d. Thus, as shown in FIG. 3, the slots 106c and 106d have wider elongate portions 109a, 109b extending from the rounded portions 107c, 107d towards the terminal ends of the leaf segments 104d, 104e. Such configuration of the slots can facilitate easier delivery of the suture removably retained on the graft preparation holder 100 to a portion of a graft.

As indicated above, each of the leaf segments 104 has an attachment end adjacent the support rail 102 and an opposite, terminal end. In the illustrated example, the leaf segments 104 are flexible such that they can bend. Each leaf segment 104 is bendable at least at a bending portion 110 disposed between the attachment end and the terminal end of the leaf segment. FIG. 3 illustrates that the leaf segments 104a, 104b, 104c, 104d, 104e have bending portions 110a, 110b, 110c, 110d, 110e, respectively. The bending portions 110a, 110b, 110c, 110d, 110e can be formed approximately at a mid-portion of the respective leaf segments such that the bending portions 110a, 110b, 110c, 110d, 110e are disposed along a same axis which can be parallel or approximately parallel to the longitudinal axis A of the support rail 102.

The bending portions 110a, 110b, 110c, 110d, 110e can be formed such that they are disposed along a different plane than the plane in which the leaf segments are disposed. For example, FIG. 1 illustrates that the bending portions of the leaf segments are disposed inwardly away from the other two portions of the leaf segments disposed on opposite sides from the respective bending portions. In the example illustrated, each of the bending portions 110a, 110b, 110c, 110d, 110e is in the form of a living hinge. However, as a person skilled in the art will appreciate, the bending portions can be formed in other manners. For example, in some embodiments, the bending portion of a leaf segment can be formed from a different material than the rest of the leaf segment and/or the bending portion can have different properties than that of the material forming the rest of the leaf segment.

Figure 4:
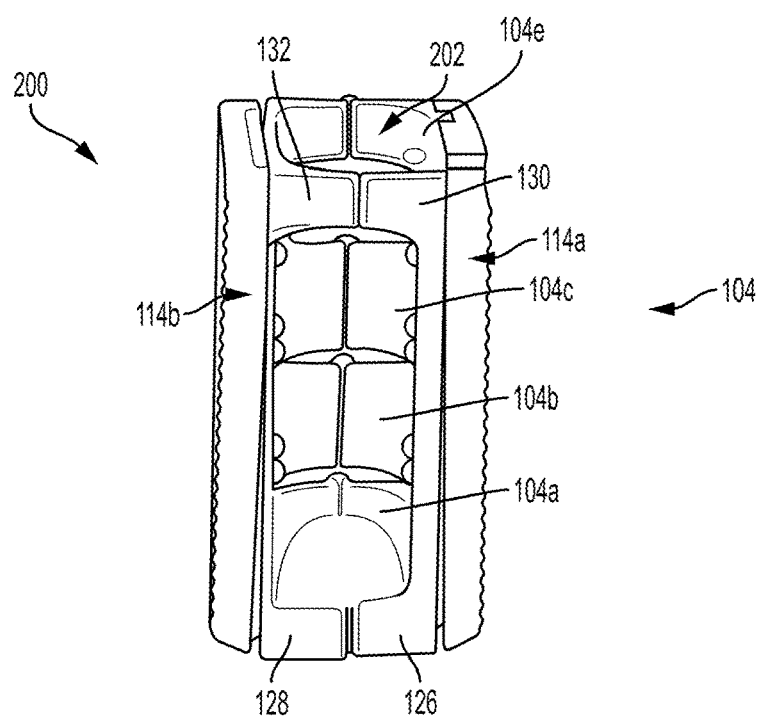
FIG. 4 is another perspective view of the graft preparation holder device of FIG. 1 in a graft holding configuration, without a suture.

The leaf segments 104 have inner and outer surfaces. In the illustrated example, the inner surfaces are surfaces of the leaf segments that define a graft receiving channel when the leaf segments are bent to form a holder having the graft receiving channel, as shown in FIG. 4 and discussed in more detail below. The outer surfaces are thus opposite surfaces that form an outer surface of the holder formed by the bent leaf segments. FIG. 1 illustrates the outer surfaces of the leaf segments 104a, 104b, 104c, 104d, 104e, with the outer surface 112o of the leaf segment 104e being labeled. FIGS. 2 and 3 illustrate the inner surfaces of the leaf segments 104a, 104b, 104c, 104d, 104e, with the inner surface 112i of the leaf segment 104e being labeled.

The graft preparation holder 100 can also include a support structure that can be secured onto the leaf segments to provide rigidity to a holder that is formed when the graft preparation holder 100 is loaded with a suture in the form of a spine and windings coupled thereto and retained over a portion of the graft to deliver the suture to the portion of the graft. Another advantageous function of the support structure is to protect the suture windings from being damaged (e.g., pinched) during a suture delivery procedure.

The support structure can have various different configurations, and it can be coupled to the leaf segments or it can remain separate from the leaf segments. In the example illustrated herein, the support structure can be in the form of first and second support panels 114a, 114b extending from the first leaf segment 104a extending from the support rail 102 adjacent to the second end 102b of the support rail 102. It should be appreciated that the leaf segment 104a is referred to as the "first" leaf segment by way of example only, as the opposite order of the leaf segments can be used alternatively. As shown in FIGS. 1-3, the first and second support panels 114a, 114b extend from the leaf segment 104a in a direction parallel to the longitudinal axis A of the support rail 102 such that the first and second support panels 114a, 114b are disposed on opposite sides of the bending portion 110a of the leaf segment 104a. The support panels 114a, 114b can be formed such that the outer edge of the support panel 114a extends along an axis that substantially coincides with the longitudinal axis A of the support rail 102, and the outer edge of the support panel 114b also extends substantially along an axis extending through the terminal ends of the leaf segments. The length of the support panels 114a, 114b, measured along an axis parallel to the longitudinal axis A, can be the same or approximately the same as the combined width of the leaf segments, such that the support panels can be folded over the leaf segments as discussed below.

Each of the first and second support panels 114a, 114b is coupled to the leaf segment 104a via a respective coupling portion 116a, 116b. The coupling portions 116a, 116b are configured such that they act as hinges at which the support panels 114a, 114b are bendable towards the leaf segments 104. The coupling portions 116a, 116b can have various configurations. In the example illustrated, the coupling portions 116a, 116b are in the form of rectangular panels. As in the example illustrated, the coupling portions 116a, 116b can be in the form of living hinges. However, other implementations of the coupling portions 116a, 116b, which can have varied widths, can be used additionally or alternatively.

Furthermore, in some implementations, the support panels can be separate elements that are not coupled to the leaf segments.

As shown, the width of the coupling portions 116a, 116b, as measured along an axis perpendicular to the longitudinal axis A, is less than the width of the support panels 114a, 114b and the leaf segment 104. The recesses formed by the coupling portions 116a, 116b offset from the outer edges of the support panels 114a, 114b, such as recesses 115a, 115b formed on both sides of the coupling 116a and shown in FIG. 2, allow clearance of the suture windings. The recess 115a provides an opening for suture tails to extend therethrough and to exit from the holder when the holder is formed. Additionally, teeth 117 can be optionally formed on the leaf segment 104a along a length thereof such that they extend into the recess 115a to be used to retain the suture tails in place. It should be appreciated that other suture-retaining elements can be formed within the recess 115a, or the recess 115a can lack any suture-retaining elements.

FIGS. 1-3 illustrate the graft preparation holder 100 in an original or unassembled configuration. The graft preparation holder 100 is designed such that its configuration can be changed to a graft holding configuration, by bending the leaf segments 104 at least at their bending portions, as shown in FIGS. 4 and 5 discussed in more detail below. As indicated above, the function of the first and second support panels 114a, 114b is to support the leaf segments 104 by making them more rigid, and to protect a suture in the graft holding configuration. As shown in FIGS. 1-3, the first and second support panels 114a, 114b have inner surfaces 118i, 120i and outer surfaces 118o, 120o, and each of the support panels 114a, 114b is bendable about the respective coupling portion 116a, 116b such that the inner surfaces 118i, 120i of the support panels 114a, 114b mate with the outer surfaces of the leaf segments 104 in the graft holding configuration, as shown in FIGS. 4 and 5.

The leaf segments 104 and the support panels 114a, 114b can have features that allow them to be mated together in the graft holding configuration. For example, as shown in FIGS. 1-3, each leaf segment 104 has at least one first mating feature that is configured to mate with at least one complementary second mating feature formed on the inner surfaces 118i, 120i of the first and second support panels 114a, 114b. In the illustrated embodiments, each of the leaf segments 104 has four female receivers, for example, female receivers or openings 122a, 122b, 122c, 122d in the leaf segment 104e. The female receivers can be through openings formed in the leaf segments 104b, 104c, 104d, 104e, or blind openings, as formed in the leaf segment 104a. The openings formed in the leaf segments 104 mate with complementary male members formed on the support panels 114a, 114b. Thus, in the example illustrated, each of the support panels 114a, 114b has a male member in the form of a protrusion configured to mate with a corresponding opening in the leaf segment. For example, the openings 122a, 122b, 122c, 122d formed in the leaf segment 104e can mate with protrusions 124a, 124b, 124c, 124d formed on the inner surfaces 118i, 120i of the first and second support panels 114a, 114b. The male members and female receivers can be in other forms, different from blind or through openings and complementary protrusions.

It should be appreciated that the first and second mating elements can have other various configurations, as the described holder is not limited to specific types of features used to mate the support panels 114a, 114b with the leaf segments 104. Each leaf segment can have any suitable number of mating elements, which can be different from the four mentioned above (e.g., there can be one, two, three, or more than four). The mating features can be integrally formed with the leaf segments or they can be coupled to the leaf segments. Also, the first and second mating elements can be of types that are different from male members and female receivers.

Figure 5A:
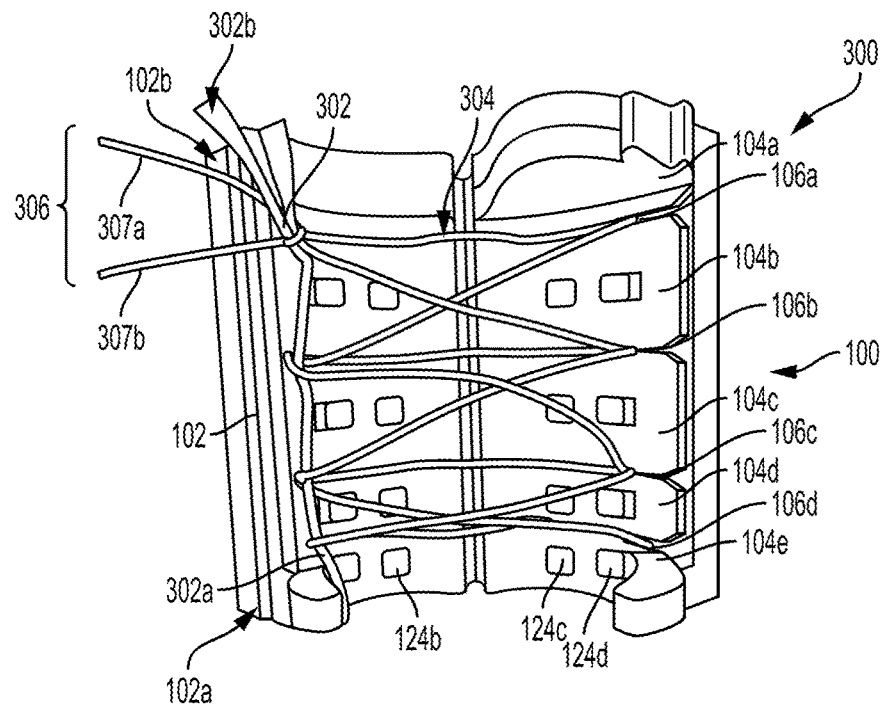
FIG. 5A is a perspective view of a graft holder construct prepared using the graft preparation holder device of FIG. 1 and a suture assembly.
Figure 5B:
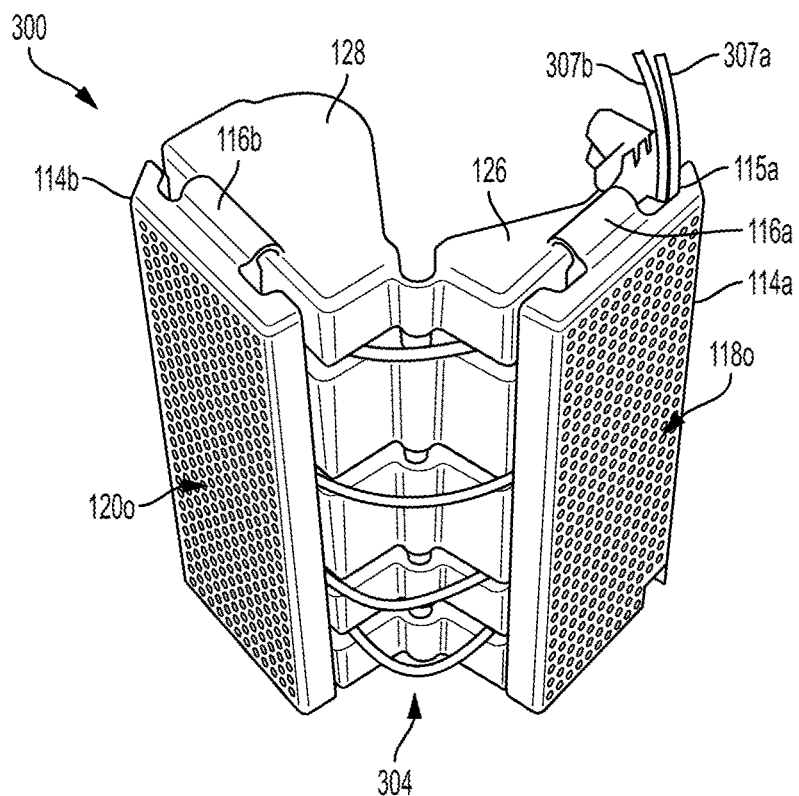
FIG. 5B is another perspective view of the graft holder construct of FIG. 5A.

The outer surfaces 118o, 120o of the support panels 114a, 114b can have surface features (e.g., bumps, ridges, bulges, grooves, protrusions, etc.), which can form uniform or non-uniform patterns over the outer surface, that form a gripping surfaces in the assembled configuration of the graft preparation holder 100. Thus, as shown in FIGS. 2 and 3, and as also illustrated in FIG. 5B, the outer surfaces 118o, 120o of the support panels 114a, 114b have small bump-like surface features. Any other surface features can be formed additionally or alternatively. Furthermore, no surfaces features can be formed in some implementations.

In some embodiments, the support structure configured to mate with leaf segments to make the segments more rigid and easier to hold, can be different from the first and second support panels 114a, 114b described herein. For example, the support structure can be in the form of a holder or other structure configured to reversibly mate with the leaf segments 104. The holder can securely fit over the leaf segments or it can be mated with the leaf segments to provide rigidity thereto in other ways.

The graft preparation holder 100 can be formed from any suitable materials, a variety of which are well known to those skilled in the art. Non-limiting examples of the materials include from polypropylene, polyethylene, nylon, acetal, and acrylonitrile butadiene styrene (ABS). A person skilled in the art will appreciate that the graft preparation holder 100 can be formed from any other materials or a combination of materials. The graft preparation holder 100 can be molded or formed using other technique(s) as known in the art.

As shown in FIGS. 1-3, in the original configuration of the graft preparation holder 100, before a holder is formed, the attachment end of each leaf segment is disposed at a distance from the terminal end of the leaf segment that is substantially equal to the length of the leaf segment, as shown in FIG. 3. As indicated above, the leaf segments 104a, 104b, 104c, 104d, 104e are configured to bend along at least the bending portions thereof to a graft holding configuration. In such graft holding configuration, as shown in FIG. 4, the terminal ends of the leaf segments are in proximity to the attachment ends of the leaf segments to thus form a graft holder 200 having a graft receiving channel 202 defined by the inner surfaces of the leaf segments.

As shown in FIG. 4, the holder 200 is formed by mating the support panels 114a, 114b with the leaf segments 104 and bending the resulting structure (in this example, manually). As shown, the holder 200 is somewhat rectangular in shape, with a substantially cylindrical cross-section, when the leaf segments are bent to bring their attachment and terminal ends together. However, it should be appreciated that the somewhat rectangular holder 200 is shown by way of example only, and a holder carrying a delivery suture assembly in accordance with embodiments described herein can have other configurations. It should be noted that FIG. 4 shows the holder 200 without a suture for illustration purposes only, since, in use, the holder 200 will have a suture spine and suture windings coupled to the spine removably retained thereon.

In the illustrated embodiment, the leaf segments include spacing elements that are matable so as to facilitate formation of the holder. For example, the spacing elements can define outer walls of a graft receiving channel in the graft holder formed from the leaf segments. The spacing elements can also be configured to hold the portion of the graft extending through the graft receiving channel.

The spacing elements can have various configurations. As shown in FIGS. 2 and 3, the first leaf segment 104a extending from the support rail 102 adjacent to the second end 102b of the support rail 102 has a first spacing element 126 and a complementary second spacing element 128. The first and second spacing elements 126, 128 extend from the leaf segment 104a in a direction perpendicular to the longitudinal axis A of the support rail 102 such that the first and second spacing elements 126, 128 are disposed on opposite sides of the bending portion 110a of the leaf segment 104a. The first and second spacing elements 126, 128 are configured to mate when the holder is formed. For example, in the illustrated embodiment, the second spacing element 128 has three ridges and two grooves on a surface facing the first spacing element 126, whereas the first spacing element 126 has two ridges and one groove on a surface facing the second spacing element 128. As shown in FIG. 4, when the leaf segments are bent and the first and second spacing elements 126, 128 are brought closer together, the groove of the first spacing element 126 receives therein the middle ridge of the second spacing element 128.

In this example, the first and second spacing elements 126, 128 are different in size such that the second spacing element 128 has a larger surface. However, it should be appreciated that the described techniques are not limited to any specific configuration of the first and second spacing elements 126, 128. Thus, the spacing elements can have other sizes and configurations, and they can be configured to mate in other various ways.

The graft preparation holder 100 can have other spacing elements. Thus, as shown in FIGS. 2 and 3, the last leaf segment 104e extending from the support rail 102 adjacent to the first end 102a of the support rail 102 has a third spacing element 130 and a complementary fourth spacing element 132. The third and fourth spacing elements 130, 132 extend from the last leaf segment 104e in a direction perpendicular to the longitudinal axis A such that the third and fourth spacing elements 130, 132 are disposed on opposite sides of the bending portion 110e of the last leaf segment 104e. The third and fourth spacing elements 130, 132 can have various configurations, for example, as in this embodiment, they can be in the form of protrusions having substantially the same configuration and size. As shown in FIG. 4, the holder 200 is formed such that the first and second spacing elements 126, 128 are mated on one end of the holder 200 and the third and fourth spacing elements 130, 132 are mated on another, opposite end of the holder 200, so as to form the graft receiving channel 202. A person skilled in the art will appreciate that one or more of the leaf segments can additionally or alternatively have other types of spacing elements. Also, one or more of the leaf segments can have other elements that facilitate formation of a holder in a graft holding configuration.

As discussed above, a graft preparation holder, such as graft preparation holder 100 in FIGS. 1-3, can be used to form a graft holder construct for removably carrying a suture to be delivered to a graft. FIGS. 5A and 5B illustrate a graft holder construct 300 formed from the graft preparation holder 100, and a suture assembly including a suture spine 302 and a plurality of windings 304 formed from a suture and spaced longitudinally along the suture spine 302. The suture spine 302 is removably seated adjacent to the elongate support rail 102 along the longitudinal axis A of the support rail 102. Each of the windings 304 is coupled to the spine 302 (e.g., by passing through the spine 302) and removably passes between adjacent leaf segments 104 such that the windings are retained within the slots 106a, 106b, 106c, 106d between the adjacent leaf segments 104. As indicated above, the slots can retain the suture windings disposed therein (e.g., by pinching the suture) due to the configuration of the slots. After the suture is assembled onto the graft preparation holder 100, the support panels are mated with the leaf segments. The resulting graft preparation holder can have any suitable size. For example, it can have a length of approximately 30 mm and a width of approximately 15 mm. However, as a person skilled in the art will appreciate, the graft preparation holder can have other suitable length and width.

The graft holder construct 300 can be formed by coupling a suture 306 to the graft holder 100. An assembly system (not shown) can be used to couple the suture 306 to the graft holder 100 to thus assemble the graft holder construct 300. The assembly system can be used to removably hold the graft preparation holder 100 (FIGS. 1-3) in an original configuration. Specifically, the graft preparation holder 100 can be coupled or otherwise associated with the assembly with the support panels 114a, 114b extending as shown in FIGS. 1-3. The elongate suture spine 302 can be seated adjacent the support rail 102 such that first and second ends 302a, 302b of the spine 302 are adjacent the first and second ends 102a, 102b of the support rail 102, as shown in FIG. 5A. The suture spine 302 can be retained in association with the holder 100 using one or more suitable retaining features. For example, in the example illustrated, as shown in FIGS. 1-3, the leaf segment 104e of the leaf segments 104 have the cleat 105 configured to removably retain the suture spine. Any other retaining features can additionally or alternatively be formed on the holder 100 for removably retaining therein the spine and/or the windings.

A person skilled in the art will appreciate that the spine 302 can have any suitable length. In the examples illustrated in FIGS. 5A and 5B, the spine 302 has approximately the same length as the holder formed after the support structure is mated with the leaf segments, or it can extend slightly beyond the holder.

The suture 306 can be coupled to a needle or other suture passing element and it can be passed through the spine 302, starting from the second end 302b of the spine. Thus, a first tail 307a of the suture 306 extends from the holder adjacent the second end 102b of the support rail 102. During assembly, the spine 302 can be seated along the support rail 102 such that, when the suture 306 is passed through the rounded portions 107a, 107b, 107c, 107d of the slots 106a, 106b, 106c, 106d, the suture 306 is thereby passed through the spine 302.

In some embodiments, the suture 306 can be passed through and around the graft preparation holder 100 in two passes to be loaded thereon in a desired manner. In the first pass, the suture 306 is sequentially passed through each of the rounded portions 107a, 107b, 107c, 107d, across the length of each of the leaf segment along its inner surface, through a portion of each of the slots 106a, 106b, 106c, 106d, and then across the length of the adjacent leaf segment along its outer surface and, finally, through the next rounded portion. Spacing features (e.g., rods or other elements) can be used in association with the assembly structure to prevent the suture from collapsing into within the slots. For example, a removable rod can be used to keep the suture in proximity to the terminal ends of the leaf segments. The spacing features allow tensioning the suture while the windings are being created around the holder. The rod can be removably inserted into appropriate openings in the assembly structure or it can otherwise be temporarily coupled with the assembly structure.

Spacing features (e.g., rods or other elements) can also be used during suture loading to keep the suture 306 a distance away from the outer surfaces of the leaf segments, such that the windings 304 are spaced from the outer surfaces. Regardless of the specific configuration of the spacing features, such features allow forming the windings in a uniform manner, such that the windings have approximately the same length and together form a suture "channel" having a size appropriate for passing a graft therethrough. For example, various spacing features (e.g., rods of different diameters) can be used to space the suture in relation to the graft preparation holder so as to create the windings appropriate for grafts ranging from about 3 mm to about 12 mm is diameter. However, a person skilled in the art will appreciate that the spacing features or other elements (either associated or not associated with the assembly structure) can be used to create windings removably coupled to the holder for a graft of any size.

Regardless of the configuration of the assembly structure and spacing elements used as discussed above, the windings are created around the graft preparation holder such that they can fit over a graft and such that they are removable from the holder.

After the first pass of the suture loading procedure, suture windings are formed along the spine 302 and around the graft preparation holder 100, from the second end 302b to the first end 302a of the spine 302. The suture 306 thus extends from the first end 302a of the spine 302.

In the second pass of the suture loading procedure, the suture 306 is passed through the spine 302 and around the graft preparation holder 100 in a similar manner but in the opposite direction, from the first end 302a of the spine 302 to the second end 302b thereof. Thus, the suture is passed through the rounded portions 107d, 107c, 107b, 107a of the slots 106d, 106c, 106b, 106a, in this order. As in the first pass, as the suture is passed through the rounded portions, it is passed through the spine 302. During the second pass, the spacing elements of the assembly structure remain associated with the graft preparation holder 100 to help creating uniform windings that are spaced in a desired manner and are retained within the slots as shown in FIG. 5A. During the second pass of the suture loading procedure, the windings are formed such that they form, together with the windings created in the first pass, a criss-cross like pattern along inner surfaces of the leaf segments, as shown in FIG. 5A. After the suture 306 reaches the second end 302b of the spine 302 as the windings are formed, a second tail 307b of the suture 306 extends adjacent the second end 102b of the support rail 102. In this way, the first and second tails 307a, 307b are disposed adjacent to one another, as shown in FIG. 5A.

The windings 304 are formed such that they are removably retained in association with the graft preparation holder 100 by being coupled to the spine 302 and by being retained within the slots between adjacent leaf segments. The windings 304 are retained in the slots due to the configuration of the slots and the configuration of the graft preparation holder. Specifically, after the windings are completed, the support panels 114a, 114b are bent and "folded" at the coupling portions 116a, 116b such that their inner surfaces are brought in proximity to the outer surfaces of the leaf segments 104. The support panels 114a, 114b are then mated to the leaf segments to maintain the suture windings in the proper configuration and to prevent premature release of the windings from the graft preparation holder. The support panels 114a, 114b provide stability to the leaf segments such that the segments do not flex or move with respect to one another during use of the graft construct.

As indicated above, each leaf segment 104 has at least one first mating feature that is configured to mate with at least one complementary second mating feature formed on the inner surfaces 118i, 120i of the first and second support panels 114a, 114b. For example, as in the illustrated embodiments, each of the leaf segments 104 has female receivers that are configured to mate with complementary male members formed on the support panels 114a, 114b. As shown in FIG. 5A, male members 124b, 124c, 124d (the male member 124a is obscured) formed on the support panels 114a, 114b are mated with the complementary female receivers (not labeled in FIG. 5A) formed on the leaf segment 104e. In the example illustrated, the support panels 114a, 114b are mated with the other leaf segments 104a, 104b, 104c, 104d using the same mating features. However, as a person skilled in the art will appreciate, the support panels and the leaf segments can be mated using other various features, as the described techniques are not limited in this respect. As another variation, more than one type of first mating features and more than one type of second mating features can be used.

FIG. 5B illustrates the graft holder construct 300 that is formed when the suture spine and windings are coupled to the holder 100 and the support panels 114a, 114b are mated with the leaf segments 104, with the outer surfaces 118o, 120o of the support panels 114a, 114b shown. The support panels 114a, 114b are disposed on opposite sides of a substantially midpoint of the leaf segments.

Sutures comprising any suitable materials can be used for the described graft preparation techniques. In some embodiments, the suture 306 forming the windings, and the suture forming the spine 302 can comprise various surgical sutures, typically size 0 to size 5, such as Orthocord™ suture commercially available from DePuy Mitek, and Ethibond™ suture available from Ethicon. In some implementations, the suture of size 2 can be used. Orthocord™ suture is approximately fifty-five to sixty-five percent PDS™ polydioxanone, which is bioabsorbable, and the remaining percent ultra high molecular weight polyethylene, while Ethibond™ suture is primarily high strength polyester. The sutures can also comprise High-Molecular Weight (HMW) polyethylene sutures or HMW polyethylene sutures with a co-braid (e.g., monofilament polypropylene, nylon or other co-braid). In some embodiments, monofilament sutures such as, for example, Monocryl® available from Ethicon, may be utilized. As another example, an absorbable suture such as Vicryl® (a copolymer made from 90% glycolide and 10% L-lactide) also available from Ethicon may be used. The sutures can include any suitable amount and type of bioabsorbable material, which can depend on a particular surgical procedure and/or surgeon preferences.

The suture(s) used in conjunction with the described techniques can have a thickness and structure appropriate for a portion of it to be threaded through the suture itself. The sutures can have multiple threads that can be combined in a suitable manner to (e.g., using braiding, weaving, knitting, entangling and/or using any other technique) such that the suture has sufficient strength and a structural integrity of the suture is maintained even if it is penetrated.

As used herein, the graft holder construct 300 includes the bendable graft preparation holder 100 and the suture assembly including the suture spine 302 with the windings 304 coupled thereto. As shown in FIG. 5B, the tails 307a, 307b of the suture 306 extend from the recess 115a (FIG. 2) of the construct 300. In use, a graft is placed within the graft holder construct 300 shown in FIGS. 5A and 5B by a surgeon to reinforce the graft and to create a construct including the graft and the suture assembly. FIGS. 6A-6E illustrate one embodiment of a method of delivering the graft holder construct 300 to a graft 600 and affixing a suture assembly 602 onto the graft 600. The suture assembly 602 includes the spine and the windings coupled thereto, such as the spine 302 and the windings 304 shown in FIGS. 5A and 5B.

The graft 600 can be a ligament graft that can be prepared using known graft preparation techniques. The graft 600 can be obtained either from the patient with the diseased or damaged ligament ("autograft") or from a donor ("allograft"). The graft 600 can include one or more tendon strands or other type of grafts. The graft 600 can be cleaned, sized and processed in other suitable ways prior to affixing sutures thereto in accordance with the described techniques.

Figure 6A:
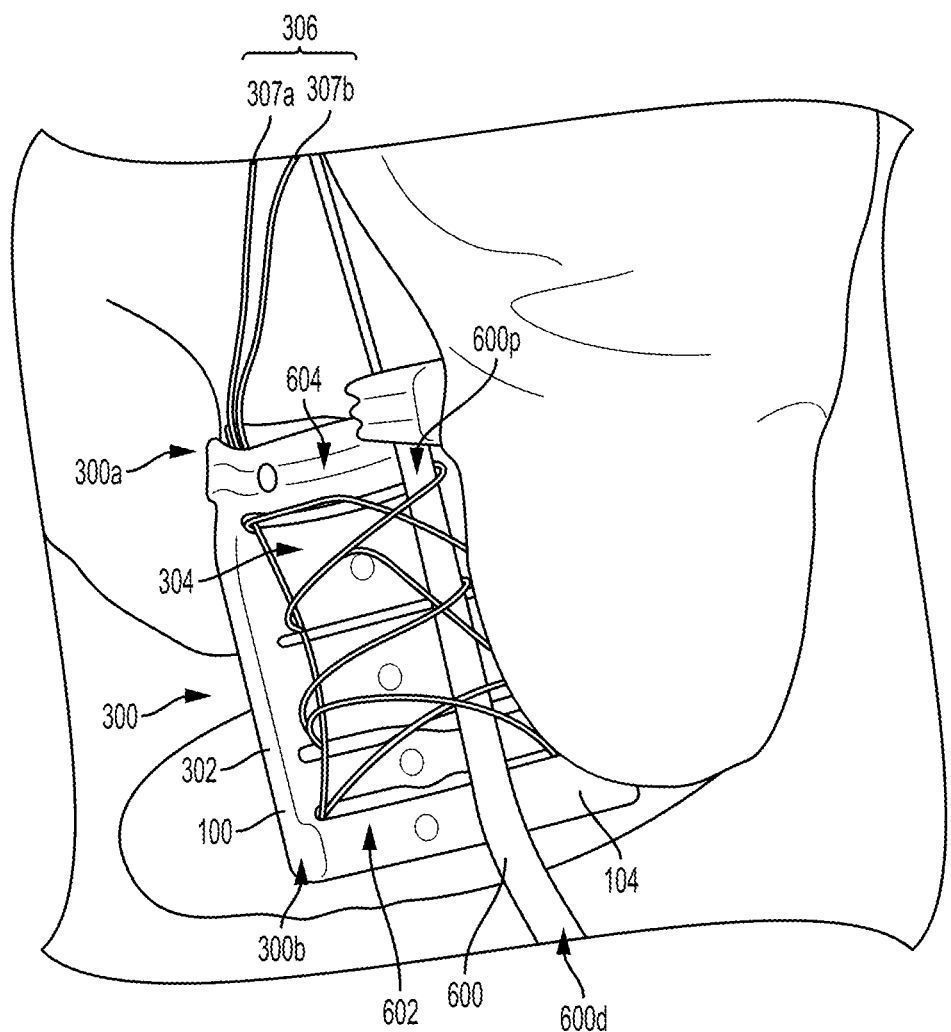
FIGS. 6A-6E are schematic illustrations of steps of preparing a graft using the graft holder construct of FIG. 5A.

As shown in FIG. 6A, the graft holder construct 300 can be first disposed over a portion of the graft 600 that is adjacent to a proximal end 600p of the graft 600. A distal portion of the graft 600d is also shown in FIG. 6A. However, it should be appreciated that only a portion of the graft 600 is shown, and that the actual distal end of the graft 600 can be located farther away from its proximal end 600p than shown in FIGS. 6A-6E. As used herein, the "proximal" end can be defined as an end of the graft 600 that is nearest surgeon's hands preparing the graft 600. The "distal" portion or end can be defined as an opposite end of the graft 600 which can be fixed using, for example, suitable graft preparation equipment (not shown). Alternatively, in some cases, the distal end of the graft 600 can remain attached to the donor site from which the graft 600 is being harvested, such that the graft 600 is prepared for the reconstruction surgery without being separated from that site.

FIG. 6A illustrates the graft holder construct 300, having first and second ends 300a, 300b, that is also shown in FIGS. 5A and 5B, associated with the graft 600 in a pre-deployment configuration. The graft holder construct 300 includes the bendable elongate holder 100 (FIGS. 1-4). Thus, components of the graft holder construct 300 are not described in connection with FIG. 6A to avoid repetition. In addition, not all of the components of the graft holder construct 300 are visible and labeled in FIG. 6A. As shown in FIG. 6A, the graft holder construct 300 can be positioned around a portion of the graft 600 adjacent to the proximal end 600p of the graft. In the example illustrated, the graft 600 is passed through a graft receiving channel 604 defined by the inner surfaces of the leaf segments 104 by passing the proximal end 600p through the graft receiving channel 604 from the second end 300b of the graft holder construct 300. The graft holder construct 300 is positioned adjacent an end of the graft 600. In the example illustrated in FIGS. 6A-6E, the graft holder construct 300 is positioned over the graft 600 adjacent the proximal end 600p thereof. However, both ends of the graft 600 are typically prepared for the ligament reconstruction or other procedure. Accordingly, the end of the graft 600 being referred to as a proximal end when the sutures are being affixed thereto can be referred to as a distal end when the sutures are applied to the opposite end of the graft.

After the graft holder construct 300 is associated with the graft 600, the bendable graft preparation holder 100 is manipulated to change its configuration from the pre-deployment configuration to the graft holding configuration. Specifically, as indicated above, the graft preparation holder 100 is manipulated to bend the leaf segments such that they assume an arc-like shape and the attachment and terminal ends of the leaf segments are brought in closer proximity to one another, so as to form a holder defining the graft receiving channel 604. An example of such a holder is shown for illustration purposes only, without a suture assembly, in FIG. 4 as holder 200.

Figure 6B:
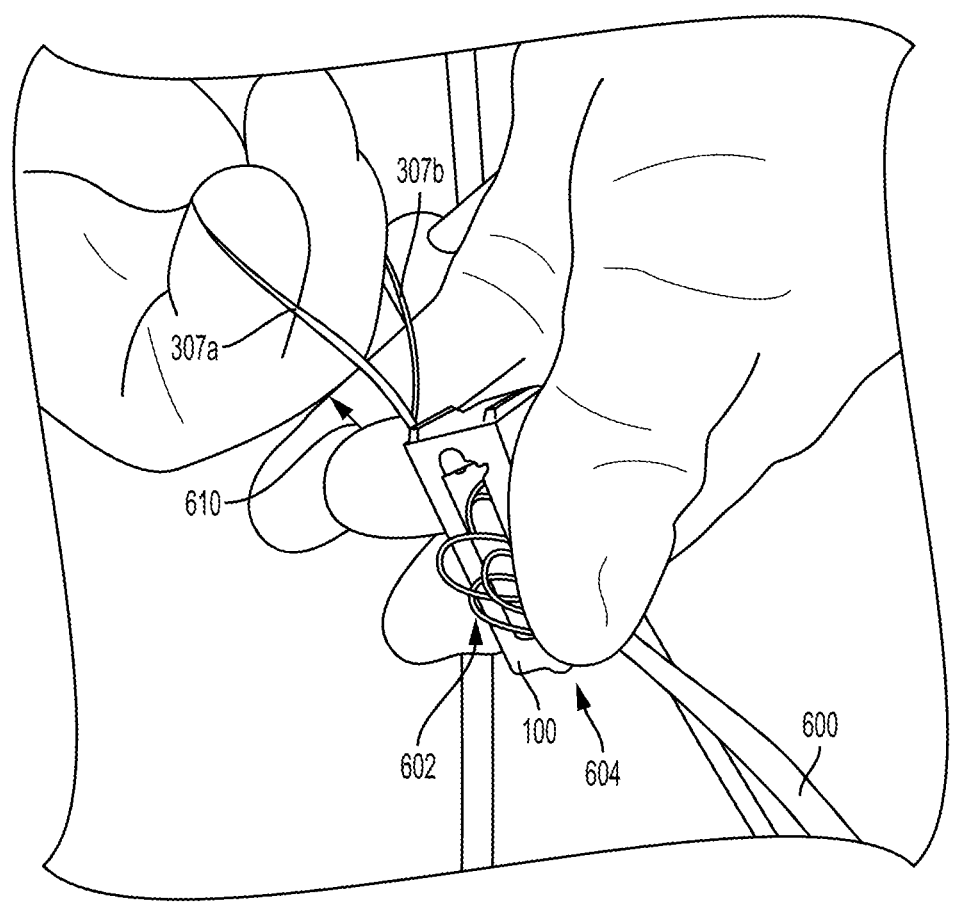

The graft preparation holder construct 300 in the graft holding configuration is shown in FIG. 6B. The graft receiving channel 604 having a substantially cylindrical configuration is formed when the leaf segments are bent along at least the bending portions thereof, for example, when the surgeon's hand is "squeezing" the graft preparation holder 100 as shown in FIG. 6B. The graft holder construct 300 acts as a graft-clamping delivery system. The support panels or other support structure(s) provide sufficient rigidity to the holder such that the holder can be grasped firmly, without a risk of causing its undesirable deformation. As mentioned above, the outer surfaces of the support panels (or other support structure, if it is used additionally or alternatively) can have surface features that facilitate grasping of the support structure by the user's hand.

In the graft holding configuration, the first and second spacing elements 126, 128 of the graft preparation holder 100 are brought together so as to clamp the graft 600 therebetween. When the graft 600 is retained in this manner in association with the graft holder construct 300 held by one hand of the surgeon, the surgeon's other hand can hold the first and second tails 307a, 307b of the suture 306. In this way, the suture assembly can be delivered to the graft by a single user, which can greatly simplify and ease the suture delivery process. Moreover, because the graft is clamped, the need for additional clamping instruments, such as hemostats or other similar instruments, can be reduced or eliminated.

Figure 6C:
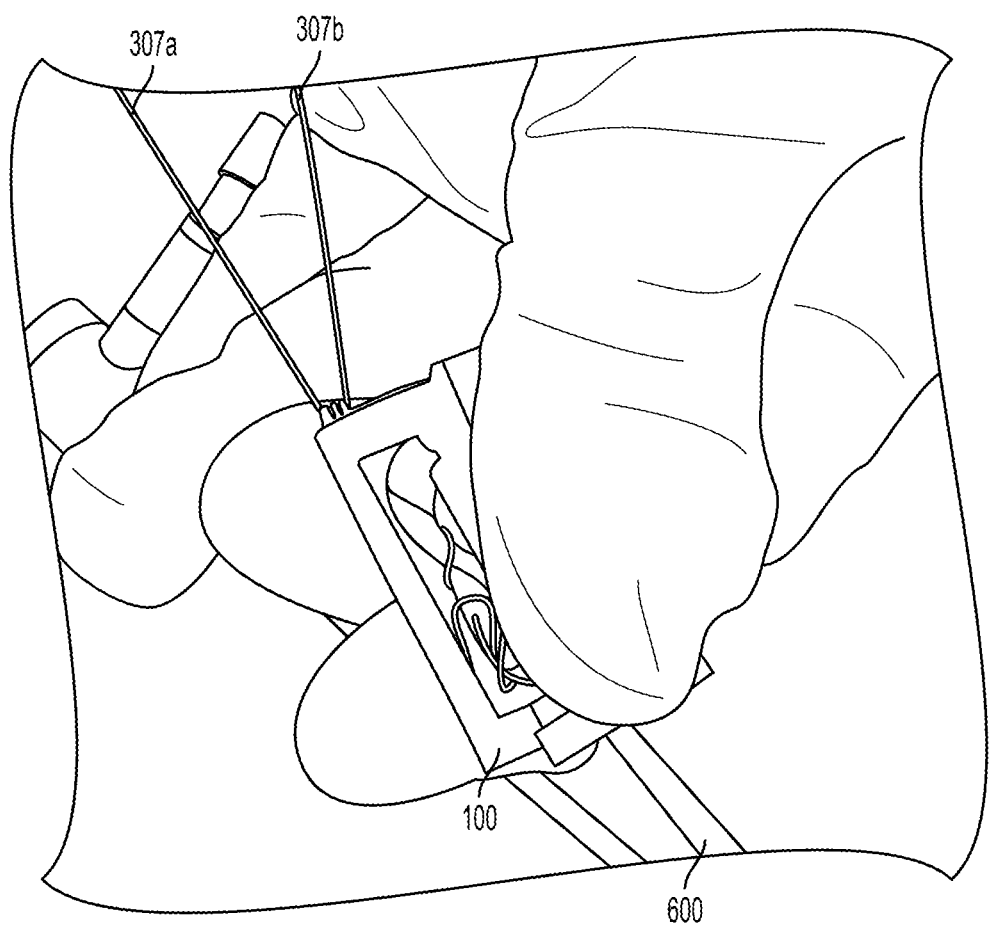

The tails 307a, 307b are then manipulated, for example, pulled in the direction away from the construct 300—i.e., proximally towards the surgeon, in a direction shown by an arrow 610 in FIG. 6B. As the tails 307a, 307b are being pulled, the windings of the suture assembly 602 separate from the holder 100 and become affixed to the portion of the graft 600, as shown in FIG. 6C. The tails 307a, 307b can be pulled in an alternating fashion, such that the windings formed by the respective portions of the suture are tightened in an alternating manner. However, the tails 307a, 307b can alternatively or additionally be pulled simultaneously, as embodiments are not limited to a specific way of manipulating the tails 307a, 307b to secure the windings around the graft.

The windings are removably coupled to the holder 100 and are configured to be released from the holder when the suture tails are appropriately manipulated in the manner discussed above. As discussed above, the slots 106a, 106b, 106c, 106d formed between the adjacent leaf segments are sufficiently narrow such that the windings are retained in the slots until tension is applied to the suture tails 307a, 307b to cause the windings to pull through the slots and thus separate from the leaf segments. Referring back to FIG. 3, in the example illustrated, the slots 106c and 106d have wider elongate portions 109a, 109b extending from the rounded portions 107c, 107d towards the terminal ends of the leaf segments 104d, 104e. As the surgeon pulls on the suture tails to separate the windings from the holder and the load thereby applied to the windings increases, such elongate portions 109a, 109b can allow for pulling the suture tails at a more advantageous angle. It should be appreciated, however, that, as mentioned above, the described techniques are not limited to any specific configuration of the slots, and that other features can be used to facilitate retention of the windings on the holder and subsequent separation of the winding therefrom.

Figure 6D:
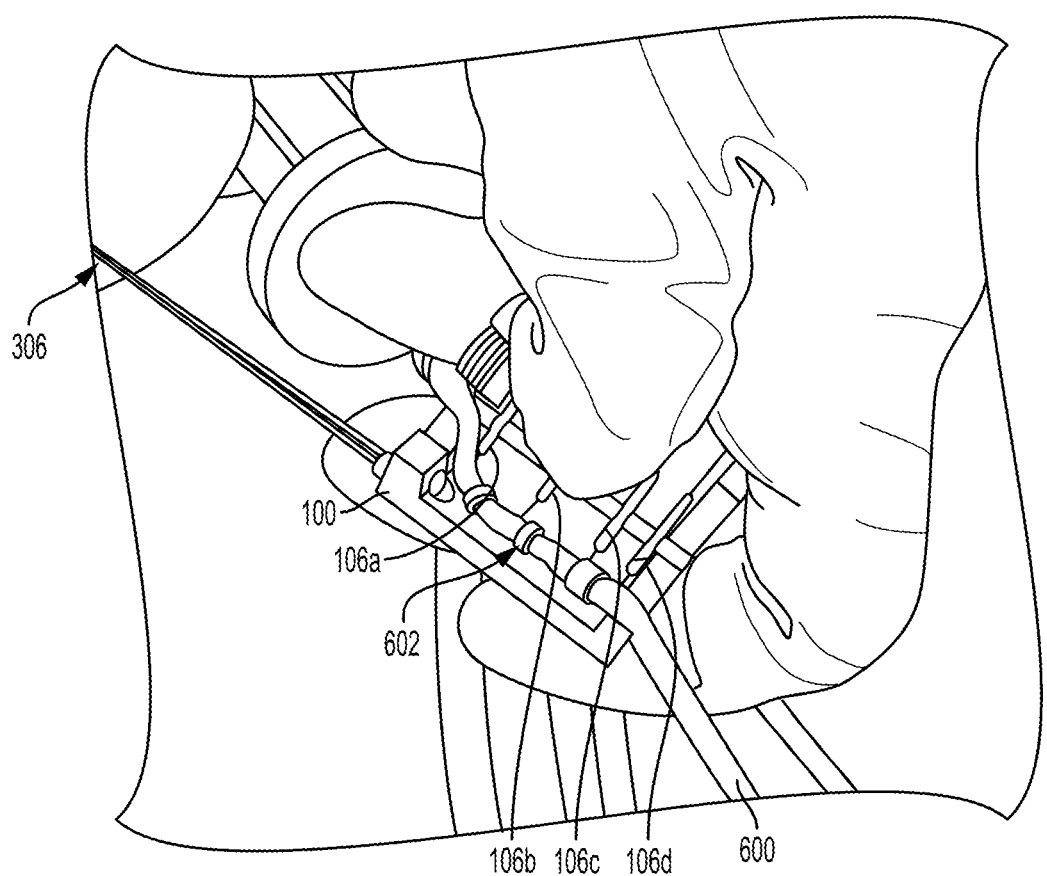
Figure 6E:
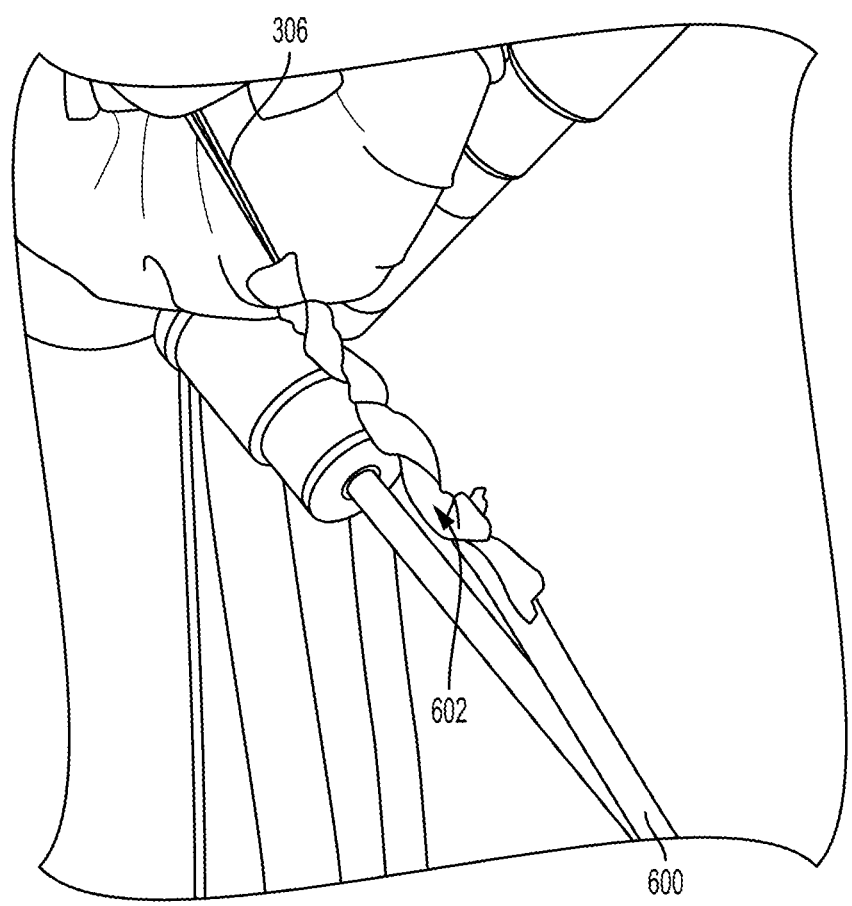

The windings are secured around the portion of the graft 600 without penetrating the graft 600 and such that they are spaced apart along a length of the portion of the graft. As the windings 304 are being separated from the holder 100, the surgeon continues holding the holder 100 so as to maintain the graft receiving channel 604, as shown in FIG. 6C. The suture spine 302 can remain associated with the holder 100 until all of the windings are affixed to the graft 600. Afterwards, the configuration of the holder 100 can be reconfigured so as to "unfold" it such that it no longer forms the graft receiving channel, as shown in FIG. 6D. The suture assembly 602 can then be separated from the holder 100 such that the spine 302 and the windings 304 are affixed to the graft 600, as shown in FIG. 6E.

It should be appreciated that although illustrated embodiments provide techniques for preparing anterior or posterior cruciate ligaments for ligament reconstruction surgery, the techniques can be adapted for preparation of other ligaments as well.

What is claimed is:

1. A method of preparing a graft for a surgical procedure, the method comprising:
   positioning a graft holder construct around a portion of the graft, the graft holder construct comprising:
     an elongate body having a support rail along one side thereof with a lateral member extending laterally from the support rail, and having a bending portion centrally located and aligned with a longitudinal axis of the elongate body; and
     a suture assembly comprising a plurality of windings that are spaced longitudinally along the support rail and a suture tail positioned adjacent to the support rail;
   changing a configuration of the elongate body so as to define a graft receiving channel formed by the lateral member and to secure the graft holder construct around the portion of the graft; and
   pulling the suture tail to affix the suture assembly to the portion of the graft such that the plurality of windings are secured around the portion of the graft without penetrating the graft and the windings are spaced apart along a length of the portion of the graft.

2. The method of claim 1, wherein the graft holder construct is configured such that, when the windings are secured around the portion of the graft, the elongate body separates from the suture assembly.

3. The method of claim 1, wherein changing a configuration of the elongate body so as to define the graft receiving channel comprises causing the lateral member to bend.

4. The method of claim 1, wherein:
   the lateral member has an attachment end at the support rail and an opposite, terminal end;
   the lateral member is bendable at the bending portion, the bending portion disposed between the attachment end and the terminal end of the lateral member; and
   wherein the changing of the configuration of the elongate body includes causing the lateral member to bend along at least the bending portion thereof such that the terminal end of the lateral member is in proximity to the attachment end of the lateral member.

5. The method of claim 1, wherein securing the graft holder construct around the portion of the graft comprises retaining the portion of the graft between first and second spacers extending from the lateral member.

6. The method of claim 1, wherein the plurality of windings form a criss-crossing pattern along the graft when secured around the portion of the graft.

7. The method of claim 1, wherein the elongate body includes a first support panel and a second support panel extending from the lateral member, and wherein the method further comprises positioning the first support panel and the second support panel at an outer surface of the lateral member such that the first support panel and the second support panel maintain a position of the lateral member.

8. The method of claim 7, wherein the lateral member includes a first mating feature configured to mate with a complementary second mating feature formed on an inner surface of one of the first support panel and the second support panel, and wherein the first mating feature engages the second mating feature when the first support panel and the second support panel are positioned at the outer surface of the lateral member.

9. A method of preparing a graft for a surgical procedure, the method comprising:
   positioning a graft holder construct around a portion of the graft, the graft holder construct comprising:
     an elongate body having a support rail along one side thereof with a lateral member extending laterally from the support rail and having a bending portion centrally located and aligned with a longitudinal axis of the elongate body, the support rail having a rail length extending along a first direction and the lateral member having a member width extending along the first direction, the rail length greater than the member width; and
     a suture assembly comprising a plurality of windings that are spaced longitudinally along the support rail and a suture tail positioned adjacent to the support rail;
   changing a configuration of the elongate body so as to define a graft receiving channel formed by the lateral member and to secure the graft holder construct around the portion of the graft; and
   pulling the suture tail to affix the suture assembly to the portion of the graft such that the plurality of windings are secured around the portion of the graft without penetrating the graft and the windings are spaced apart along a length of the portion of the graft.

10. The method of claim 9, wherein the graft holder construct is configured such that, when the windings are secured around the portion of the graft, the elongate body separates from the suture assembly.

11. The method of claim 9, wherein changing a configuration of the elongate body so as to define the graft receiving channel comprises causing the lateral member to bend.

12. The method of claim 9, wherein:
   the lateral member has an attachment end at the support rail and an opposite, terminal end;
   the lateral member is bendable at the bending portion, the bending portion disposed between the attachment end and the terminal end of the lateral member; and
   wherein the changing of the configuration of the elongate body includes causing the lateral member to bend along at least the bending portion thereof such that the terminal end of the lateral member is in proximity to the attachment end of the lateral member.

13. The method of claim 9, wherein securing the graft holder construct around the portion of the graft comprises retaining the portion of the graft between first and second spacers extending from the lateral member.

14. The method of claim 9, wherein the plurality of windings form a criss-crossing pattern along the graft when secured around the portion of the graft.

15. The method of claim 9, wherein the elongate body includes first and second support panels extending from the lateral member, and wherein the method further comprises positioning the first and second support panels at an outer surface of the lateral member such that the first and second support panels maintain a position of the lateral member.

16. The method of claim 15, wherein the lateral member includes a first mating feature configured to mate with a complementary second mating feature formed on an inner surface of one of the first and second support panels, and wherein the first mating feature engages the second mating feature when the first and second support panels are positioned at the outer surface of the lateral member.

17. A method of preparing a graft for a surgical procedure, the method comprising:
  positioning a graft holder construct around a portion of the graft, the graft holder construct comprising:
    an elongate body having a support rail along one side thereof with a lateral member extending laterally from the support rail in a first direction and having a bending portion centrally located and aligned with a longitudinal axis of the elongate body, the lateral member having a thickness that varies along the first direction; and
    a suture assembly comprising a plurality of windings that are spaced longitudinally along the support rail and a suture tail positioned adjacent to the support rail;
  changing a configuration of the elongate body so as to define a graft receiving channel formed by the lateral member and to secure the graft holder construct around the portion of the graft; and
  pulling the suture tail to affix the suture assembly to the portion of the graft such that the plurality of windings are secured around the portion of the graft without penetrating the graft and the windings are spaced apart along a length of the portion of the graft.

18. The method of claim 17, wherein the graft holder construct is configured such that, when the windings are secured around the portion of the graft, the elongate body separates from the suture assembly.

19. The method of claim 17, wherein:
  the lateral member has an attachment end at the support rail and an opposite, terminal end;
  the lateral member is bendable at the bending portion, the bending portion disposed between the attachment end and the terminal end of the lateral member; and
  wherein the changing of the configuration of the elongate body includes causing the lateral member to bend along at least the bending portion thereof such that the terminal end of the lateral member is in proximity to the attachment end of the lateral member.

20. The method of claim 17, wherein the plurality of windings form a criss-crossing pattern along the graft when secured around the portion of the graft.

* * * * *